US 6,666,834 B2

(12) United States Patent
Restle et al.

(10) Patent No.: US 6,666,834 B2
(45) Date of Patent: Dec. 23, 2003

(54) METHOD AND APPARATUS FOR GENERATING SHOCK WAVES

(75) Inventors: Karl-Heinz Restle, Kreuzlingen (DE); Frank Schock, Constance (DE)

(73) Assignee: HMT High Medical Technologies AG, Lengwil (CH)

( * ) Notice: Subject to any disclaimer, the term of this patent is extended or adjusted under 35 U.S.C. 154(b) by 0 days.

(21) Appl. No.: 10/044,838

(22) Filed: Jan. 11, 2002

(65) Prior Publication Data

US 2002/0169397 A1 Nov. 14, 2002

(30) Foreign Application Priority Data

Jan. 11, 2001 (DE) .......................................... 101 00 974

(51) Int. Cl.[7] .................................................. A61N 7/00
(52) U.S. Cl. ................................ 601/2; 601/4; 367/147
(58) Field of Search ........................ 601/2–4; 600/439; 367/147, 141, 142, 481; 106/316

(56) References Cited

U.S. PATENT DOCUMENTS

| 4,721,530 A | * | 1/1988 | Ettlinger et al. ............. 106/491 |
| 5,287,856 A | | 2/1994 | Treiber ................... 128/660.03 |
| 6,080,119 A | | 6/2000 | Schwarze et al. ............... 601/4 |
| 6,092,722 A | | 7/2000 | Heinrichs et al. ............ 235/375 |
| 6,113,560 A | | 9/2000 | Simnacher ..................... 601/4 |

FOREIGN PATENT DOCUMENTS

| DE | 3542240 A1 | * | 6/1987 |
| DE | 44 00 039 | | 1/1994 |
| GB | 1073739 | | 6/1967 |

* cited by examiner

Primary Examiner—Ruth S. Smith
(74) Attorney, Agent, or Firm—Samuels, Gauthier & Stevens LLP

(57) ABSTRACT

A device for generating shock waves, specifically for medical applications, has electrodes arranged in a liquid medium, a high voltage being applied to the electrodes to generate an electrical breakdown. Particles added in powder form are suspended in the liquid medium. In order to maintain the particles in suspension, a thixotropic additive is added to the liquid medium.

23 Claims, 1 Drawing Sheet

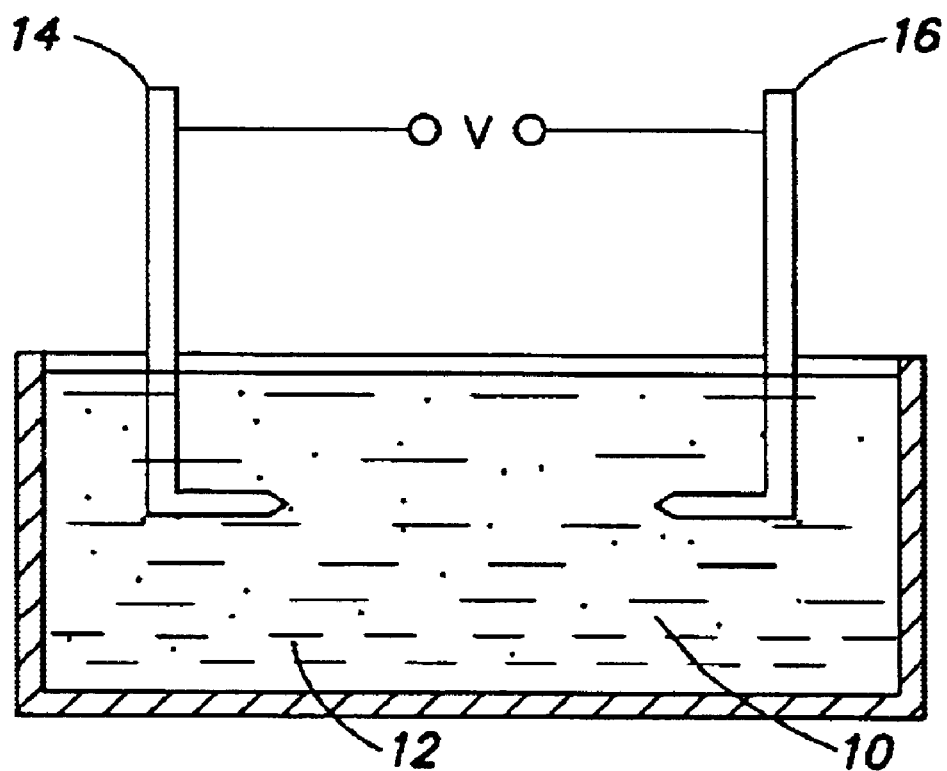

METHOD AND APPARATUS FOR GENERATING SHOCK WAVES

BACKGROUND OF THE INVENTION

The present invention relates to the field of devices for generating shock waves for medical applications, and in particular to a device for generating shock waves for medical applications that includes electrodes that are located in a liquid medium and driven to generate an electrical breakdown between the electrodes, where the medium has a structural viscosity with a thixotropic index greater than one.

Shock waves are increasingly employed in medicine, for example for breaking up concretions in the body, for stimulating bone formation, for treating orthopedic diseases, and for combating pain. To generate shock waves, devices are often used in which two electrodes are arranged a certain distance apart in a liquid medium. A high electric voltage is applied to the electrodes until an electrical breakdown results within the liquid medium. The heat developed from the electrical breakdown causes the liquid medium to vaporize, thereby creating the pressure wave. U.S. Pat. Nos. 6,080,119 and 6,113,560 both disclose devices for generating shock waves.

The action of triggering the spark discharge causing the electrical breakdown depends on the high voltage applied and the distance between the electrodes. To ensure reliable triggering of the spark discharge even at the critical distance between the electrodes, conducting, semiconducting, or polarizable particles in powder form may be added to the liquid aqueous medium. See for example U.S. Pat. No. 6,113,560 assigned to assignee of the present invention. However, the gas formed during the spark discharge may impair the formation of subsequent spark discharges, and specifically impede the propagation of the shock wave. A known remedy disclosed in published German patent application DE 197 18 451 A1 is to add a powdered catalyst to the liquid medium that reduces the gas formation and promotes the recombination of the gases formed. Both the particles promoting the spark discharge and the particles of the catalyst are added in powdered form and suspended in the liquid medium.

To ensure that the particles have the desired effect, they must be suspended specifically in the vicinity of the electrodes. Counteracting this suspension is gravity which, over time, causes the particles increasingly to settle on the bottom of the container holding the liquid medium. A lowering of the concentration of the particles promoting discharge in the vicinity of the electrodes may impair or completely impede the triggering of the spark discharge. A lowering of the concentration of the suspended catalyst particles in the vicinity of the electrodes may also result in premature formation of gas, which will delay the formation of the spark discharge and reduce the generation of pressure.

To counteract the undesirable settling of the suspended particles, the volume of liquid surrounding the electrodes may be restricted by adding a hood. Although the particles still settle due to gravity, they are agitated by each discharge and again are dispersed in suspension. Several discharges may be required, however, until the optimal suspension for operating the shock-wave source is reached. In addition, the initial voltage employed must be higher in order to achieve this first electrical breakdown. Only after the particles promoting the breakdown are sufficiently suspended can the voltage be returned to its normal operating level.

Another approach is to store the powder particles in an ancillary container, which is introduced into the volume of the liquid medium. Upon each discharge, particles are released from this container by the resulting pressure wave and enter the suspension.

Both approaches have the disadvantage that additional components (e.g., hood, or a storage container) are required that must be introduced into the volume of the liquid medium. In addition to the extra design and materials expense, these components disturb the propagation of the generated shock wave. Additionally, the shock-wave source does not immediately achieve the optimum properties at start-up.

Therefore, there is a need for a device for generating shock waves in which the particles suspended in the liquid medium may be retained in the vicinity of the electrodes without the extra design and materials expense and without impeding the generation of the shock waves.

SUMMARY OF THE INVENTION

Briefly, according to an aspect of the present invention, a device for generating shock waves for medical uses by a high voltage electrical discharge, includes a pair of electrical spark charge electrodes and a liquid medium disposed between the electrodes. A catalyst is dispersed in the liquid medium. An inorganic silicon compound is also added to the liquid medium, wherein the liquid medium containing the catalyst and the inorganic silicon compound includes a structural viscosity with a thixotropic index greater than one.

According to another aspect of the invention, a liquid medium for use in a device for generating shock waves for medical uses by applying a voltage between electrodes located within the liquid medium, comprises water and a catalyst dispersed in the water. An inorganic silicon compound is added to the water, wherein the liquid medium includes a structural viscosity with a thixotropic index greater than one.

The structural viscosity of the liquid medium is obtained by adding an inorganic silicon compound, such as silicic acid. A preferred additive is a highly dispersed silicic acid.

The highly dispersed silicic acid does not significantly affect the electrical properties of the liquid medium. The conductivity of the liquid medium, the latency period required for the formation of the electrical breakdown, and the quantity of the charge flowing from the breakdown all remain unaffected by the added silicic acid. In addition, silicic acid is heat-resistant and chemically stable—with the result that the properties of the structural viscosity are not destroyed by the plasma created during breakdown. The metal alloy of the electrodes is also not corroded by the added silicic acid.

These and other objects, features and advantages of the present invention will become more apparent in light of the following detailed description of preferred embodiments thereof, as illustrated in the accompanying drawings.

BRIEF DESCRIPTION OF THE DRAWINGS

The FIGURE is a simplified pictorial illustration of a fluid container that includes a liquid medium, a catalyst, an additive and a pair of electrodes located within the liquid medium.

DETAILED DESCRIPTION OF THE INVENTION

The FIGURE is a simplified pictorial illustration of a container that includes a liquid medium (e.g., water) containing an additive 10, and a catalyst 12. The liquid medium containing the catalyst and the additive is used in a device for generating shock waves for medical uses by applying a voltage V between electrodes 14, 16 located within the liquid medium. Devices for generating shock waves for medical uses by applying a voltage between electrodes are disclosed is U.S. Pat. Nos. 6,080,119 and 6,113,560, both assigned to the assignee of the present invention.

The additive is preferably an inorganic silicon compound that is added to the liquid medium, wherein the resulting mixture of the liquid medium, catalyst and silicon compound has a structural viscosity with a thixotropic index greater than one.

Structural viscosity here means that the viscosity of the liquid medium decreases as the velocity gradient within the liquid increases. This means that the viscosity falls when the liquid medium is moved. When the velocity gradient in the liquid medium decreases, i.e., when the liquid medium comes to rest, the viscosity again rises significantly due to thixotropy. The thixotropic index here is a measure of the structural viscosity and is defined as the ratio of the viscosity at two different velocity gradients, specifically the ratio of the viscosity at one velocity gradient relative to a velocity gradient ten (10) times greater.

This thixotropy property of the liquid medium maintains the particles in suspension in the liquid medium over a longer period of time and impedes their settling to the bottom under the influence of gravity. When the device is not in operation, the liquid medium is at rest and has a high viscosity. This high viscosity maintains the added particles in uniform suspension for an extended period of time such that the device remains in a state ready to operate and with full functional performance even after an extended period of non-use. The liquid medium is moved by the electric discharge during formation of the shock waves such that the viscosity drops significantly due to the thixotropy property. Therefore, the propagation of pressure waves within the liquid medium is not impeded by the thixotropic additive.

The structural viscosity of the liquid medium is advantageously obtained by adding an inorganic silicon compound, specifically silicic acid. The preferred additive is a highly dispersed silicic acid.

The highly dispersed silicic acid added in the form of amorphous silicon dioxide particles forms a three-dimensional network in the liquid medium through agglomeration, with the network producing the high viscosity in the quiescent state. This also has the additional advantage that the particles suspended in the liquid medium are kept a certain distance apart by the network of highly dispersed silicic acid, thereby preventing the suspended particles from conglomerating and, specifically, preventing the surface area important to the catalytic action from being reduced.

The following example illustrates the mode of action of the invention: a catalyst in the form of 0.4 g of palladium on activated charcoal is added to a volume of approximately 18 ml of liquid. The addition of 0.2 g of highly dispersed silicic acid (HDK V15 from Wacker Chemie GmbH) results in the sedimentation rate of the suspended catalyst being reduced by a factor of at least 10 to 20. Even after a standing time of more than 10 minutes, the shock-wave source is triggered immediately at the lowest power level. Without the addition of the silicic acid, the shock-wave source is no longer triggered and must be "primed" at considerably higher high-voltage levels.

Although the present invention has been shown and described with respect to several preferred embodiments thereof, various changes, omissions, and additions to the form and detail thereof may be made therein, without departing from the spirit and scope of the invention.

What is claimed is:

1. A component for use in a medical device for generating acoustic shockwaves, said component comprising: a liquid medium, electrodes located in the liquid medium, and catalyst particles added in powder form to the liquid medium, wherein the liquid medium also includes an additive such that said liquid medium containing said catalyst and said additive has a structural viscosity with a thixotropic index greater than one.

2. The component of claim 1, wherein said additive comprises a thixotropic additive.

3. The component of claim 2, wherein said additive comprises an inorganic silicon compound.

4. The component of claim 3, wherein said additive comprises silicic acid.

5. The component of claim 4, wherein said additive comprises highly dispersed silicic acid.

6. A component for use in a medical device for generating acoustic shockwaves, said component comprising:
   a pair of electrodes;
   a liquid medium disposed between said electrodes; and
   a catalyst dispersed in said liquid medium; and
   an inorganic silicon compound added to said liquid medium, wherein said liquid medium containing said catalyst and said inorganic silicon compound includes a structural viscosity with a thixotropic index greater than one.

7. The component of claim 6, wherein said inorganic silicon compound comprises silicic acid.

8. The component of claim 6, wherein said inorganic silicon compound comprises dispersed silicic acid.

9. The component of claim 6, wherein said inorganic silicon compound comprises highly dispersed silicic acid.

10. The component of claim 9, wherein said catalyst comprises palladium on activated charcoal.

11. The component of claim 10, wherein said liquid medium comprises water.

12. The component of claim 11, wherein said concentration of highly dispersed silicic acid is about 11 mg per ml of water.

13. A component for use in a medical device for generating acoustic shockwaves, said component comprising: a liquid medium, electrodes located in the liquid medium, and catalyst particles with said liquid medium, wherein said liquid medium also includes an additive such that said liquid medium containing said catalyst and said additive has a structural viscosity with a thixotropic index greater than one and the catalyst particles remain in proximity to said electrodes following an electrical discharge between said electrodes in response to a high voltage applied to said electrodes.

14. The component of claim 13, wherein said additive comprises an inorganic compound.

15. The component of claim 13, wherein said additive comprises an inorganic silicon compound.

16. The component of claim 13, wherein said additive comprises silicic acid.

17. The component of claim 13 wherein said additive comprises dispersed silicic acid.

18. A method of generating acoustic shock waves in a modified liquid medium, said method comprising:
   introducing an additive to a liquid medium including a catalyst contained within a device, that includes electrodes, for generating shockwaves to provide a modified liquid medium contained within the device, wherein the resultant modified liquid medium has a structural viscosity with a thixotropic index greater than one.

19. The method of claim 18, wherein the additive comprises a thixotropic additive.

20. The method of claim 18, wherein the additive comprises an inorganic compound.

21. The method of claim 18, wherein the additive comprises an inorganic silicon compound.

22. The method of claim 18 wherein the additive comprises silicid acid.

23. The method of claim 18, wherein the additive comprises dispersed silicic acid.

* * * * *